(12) United States Patent
Mueller et al.

(10) Patent No.: US 8,413,514 B2
(45) Date of Patent: Apr. 9, 2013

(54) METHOD FOR MANUFACTURING AN ULTRASONIC TRANSDUCER FOR USE IN A FLUID MEDIUM

(75) Inventors: Roland Mueller, Steinheim (DE); Gerhard Hueftle, Aspach (DE); Michael Horstbrink, Stuttgart-Feuerbach (DE); Tobias Lang, Stuttgart (DE); Sami Radwan, Stuttgart (DE); Bernd Kuenzl, Schwieberdingen (DE); Roland Wanja, Markgroeningen (DE)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 13/151,049

(22) Filed: Jun. 1, 2011

(65) Prior Publication Data

US 2011/0308317 A1 Dec. 22, 2011

(30) Foreign Application Priority Data

Jun. 16, 2010 (DE) .......................... 10 2010 030 189

(51) Int. Cl.
*G01N 29/02* (2006.01)
*H04R 31/00* (2006.01)

(52) U.S. Cl. ............................... 73/632; 73/644; 29/594

(58) Field of Classification Search .................... 73/644, 73/632, 861.18; 310/338, 327, 334–337; 29/594

See application file for complete search history.

(56) References Cited

U.S. PATENT DOCUMENTS

| | | | | |
|---|---|---|---|---|
| 4,297,607 | A * | 10/1981 | Lynnworth et al. | 310/334 |
| 4,774,626 | A * | 9/1988 | Charboneau et al. | 361/283.4 |
| 4,972,390 | A * | 11/1990 | Pagliarini, Jr. | 367/158 |
| 6,351,928 | B2 * | 3/2002 | Torre | 53/556 |
| 6,504,289 | B2 * | 1/2003 | Toda et al. | 310/334 |
| 7,397,168 | B2 * | 7/2008 | Straub et al. | 310/338 |
| 7,905,844 | B2 * | 3/2011 | Desilets et al. | 601/2 |
| 7,954,387 | B1 * | 6/2011 | Furlong | 73/861.28 |
| 2005/0154313 | A1 * | 7/2005 | Desilets et al. | 600/459 |
| 2011/0277557 | A1 * | 11/2011 | Kroemer et al. | 73/861.18 |

FOREIGN PATENT DOCUMENTS

| | | |
|---|---|---|
| DE | 203 02 582 | 6/2003 |
| DE | 10 2007 010 500 | 9/2008 |
| DE | 10 2008 055 116 | 7/2010 |
| DE | 10 2008 055 126 | 7/2010 |
| DE | 10 2009 046 146 | 5/2011 |
| DE | 10 2009 046 147 | 5/2011 |
| DE | 10 2009 046 149 | 5/2011 |
| EP | 0 766 071 | 4/1997 |

* cited by examiner

*Primary Examiner* — J M Saint Surin
(74) *Attorney, Agent, or Firm* — Kenyon & Kenyon LLP

(57) ABSTRACT

A method for manufacturing an ultrasonic transducer for use in a fluid medium is described. The ultrasonic transducer includes at least one transducer core having at least one acoustic-electric transducer element. The ultrasonic transducer furthermore includes at least one housing which at least partially surrounds the transducer core and which has at least one opening facing the fluid medium. In the method, at least one sealing film is stretched and connected to the housing in the stretched state in such a way that the sealing film at least partially seals the opening.

14 Claims, 3 Drawing Sheets

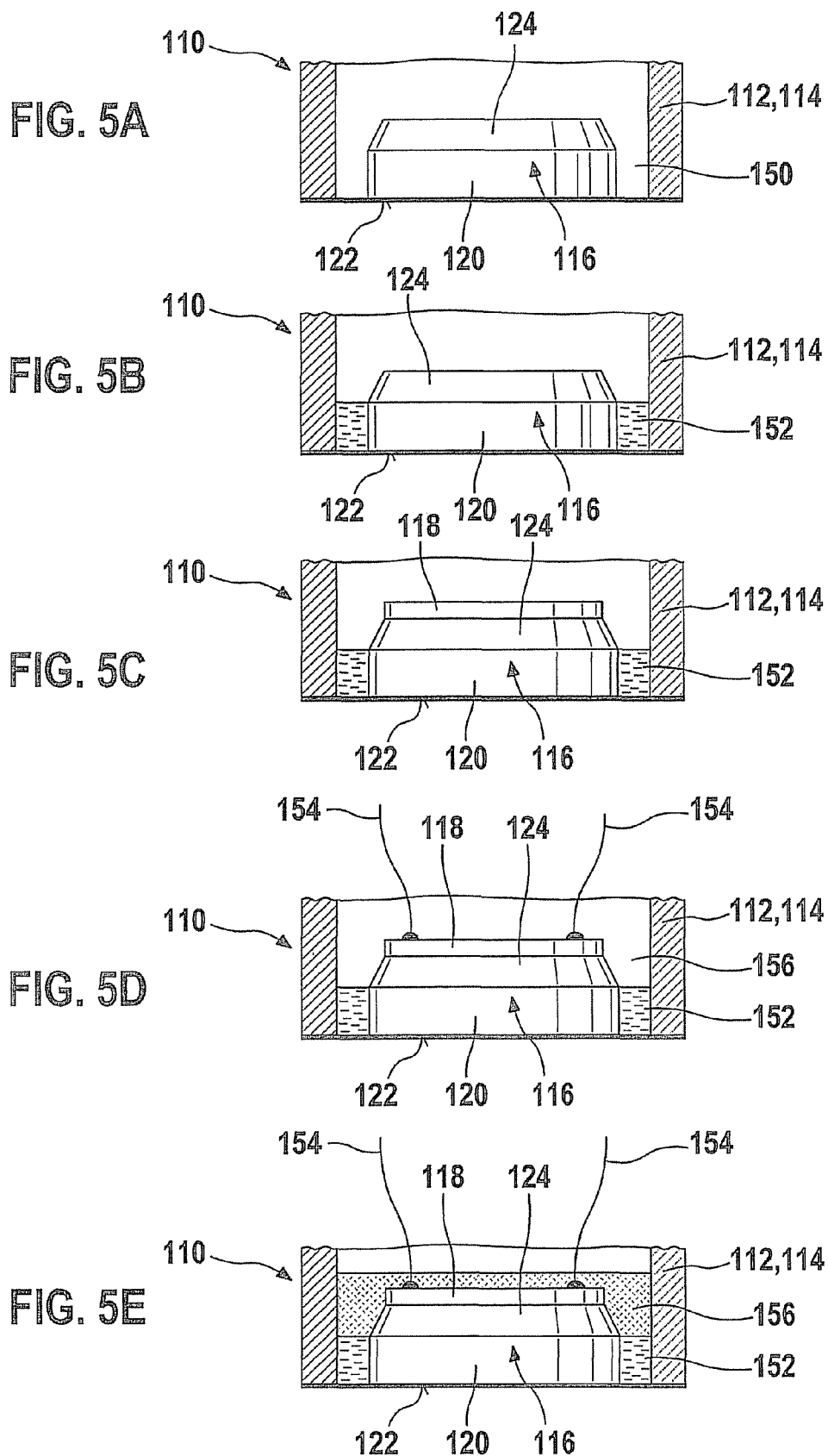

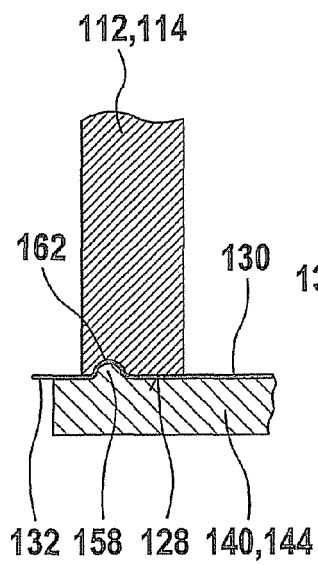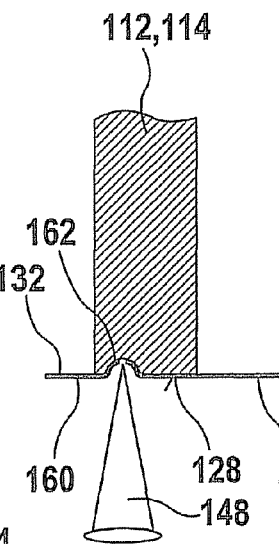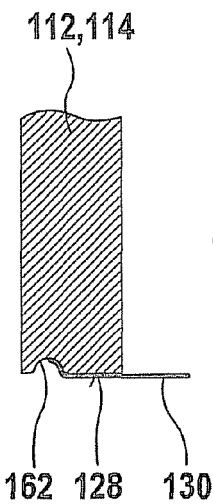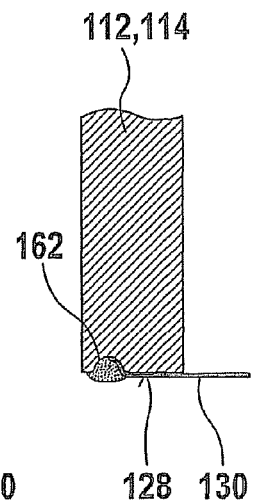
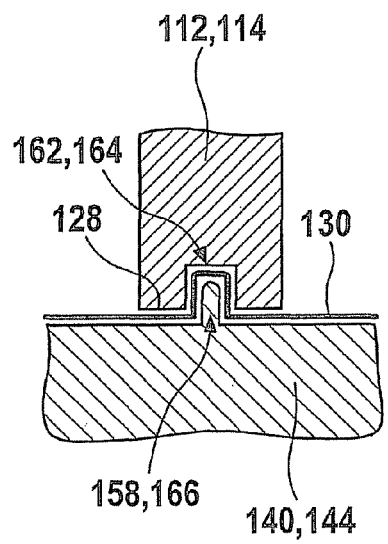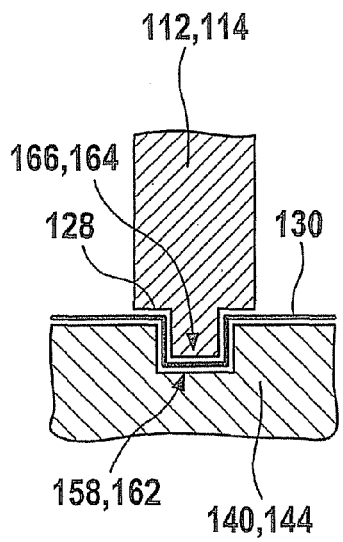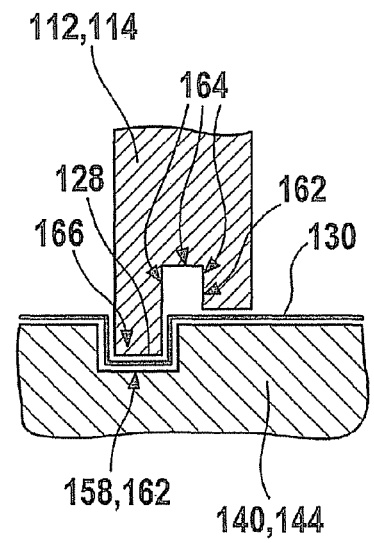

METHOD FOR MANUFACTURING AN ULTRASONIC TRANSDUCER FOR USE IN A FLUID MEDIUM

RELATED APPLICATION INFORMATION

The present application claims priority to and the benefit of German patent application no. 10 2010 030 189.2, which was filed in Germany on Jun. 16, 2010, the disclosure of which is incorporated herein by reference.

FIELD OF THE INVENTION

The present invention relates to a method for manufacturing an ultrasonic transducer for use in a fluid medium.

BACKGROUND INFORMATION

Ultrasonic transducers for use in various applications are discussed in the related art. Ultrasonic transducers are used, for example, in fluid media such as gases and/or liquids to measure a fill level and/or a flow property, for example a mass or volumetric flow, or a velocity of the fluid medium. In particular, ultrasonic transducers of this type are used in the intake tract and/or exhaust gas tract of internal combustion engines. As an alternative or in addition, ultrasonic transducers may also be used, for example, as distance sensors in air or other gases or liquids. Examples of ultrasonic transducers are discussed in DE 203 02 582 U1, EP 0 766 071 A1 or in DE 10 2007 010 500 A1.

Ultrasonic transducers may have at least one electric-acoustic transducer element, for example a piezoelectric transducer element, which is configured to convert electrical signals to ultrasonic signals and vice versa. Ultrasonic transducers are known from the related art which are based on a piezoceramic and which may additionally include at least one impedance matching layer, for example a λ/4 impedance matching layer, the electric-acoustic transducer element and the at least one optional impedance matching layer forming a transducer core. This transducer core may be introduced into a housing, for example a housing sleeve. The housing usually has at least one opening which faces the fluid medium and which may also be referred to as the radiation opening. To seal the housing interior, in which the transducer core is usually accommodated, against the fluid medium, it is believed to be understood, in principle, to apply a sealing film to this opening.

For example, post-published DE 10 2008 055 126.0, DE 10 2008 055 116.3, DE 10 2009 046 149.3, DE 10 2009 046 146.9 and DE 10 2009 046 147.7 discuss ultrasonic transducers of this type, in which a radiation opening is sealed by a sealing film. Since the sealing film itself represents an important interface of the connection between the transducer core and the fluid medium, whose quality is crucial for the radiation characteristic of the ultrasonic transducer, there remains a need for a reliable connection between a sealing film and an ultrasonic transducer housing, in particular for the purpose of measuring ultrasonic air masses in internal combustion engines, but also for other applications.

SUMMARY OF THE INVENTION

A method for manufacturing an ultrasonic transducer for use in a fluid medium, in particular a gas and/or a liquid, is proposed, as well as an ultrasonic transducer which may be manufactured according to the method according to the present invention. The ultrasonic transducer includes at least one housing and at least one transducer core which is at least partially accommodated in the housing. A housing is understood to be a structure which has an at least partially closed or possibly a partially open inner space, for example a cavity. The housing may be designed, for example, in the shape of a sleeve, in particular at least largely rotationally symmetrical. As an alternative or in addition, the housing may be designed, for example, as a frame, as a ring or as a cup, or it may include a frame, a ring or a cup. The housing may perform, in particular, the function of protecting the components of the ultrasonic transducer accommodated in the inner space of the housing against mechanical and/or chemical influences. The housing may be made, for example, of a plastic and/or a metallic material. However, ceramic housings may, in principle, also be implemented.

The transducer core includes at least one acoustic-electric transducer element. An electric-acoustic transducer element is understood to be an element which is configured to convert acoustic signals, for example ultrasonic signals, into electrical signals and/or vice versa. In particular, the acoustic-electric transducer element may be at least one piezoelectric transducer element, for example a piezoceramic, which may be having two or more electrodes. In principle, however, other embodiments are also conceivable. Furthermore, the transducer core may include at least one impedance matching body, for example at least one impedance matching layer, for example an impedance matching layer as described in the aforementioned related art. This impedance matching layer may have an acoustic impedance which lies between the impedance of the acoustic-electric transducer element and that of the fluid medium, ideally at the geometric mean of these acoustic impedances. In addition, further elements may be provided in the transducer core, for example one or more thermal matching layers which are configured, for example, to match a coefficient of expansion of the acoustic-electric transducer element to a coefficient of expansion of an impedance matching layer or of an impedance matching body in general. Structures of this type are also known.

Thus, the transducer core may have, for example, a multi-part structure which includes the acoustic-electric transducer element and the optional impedance matching body on the side of the acoustic-electric transducer element facing the fluid medium as well as, also optionally, at least one thermal matching body between the impedance matching body and the acoustic-electric transducer element. Examples are explained in greater detail below.

The housing has at least one opening facing the fluid medium. This opening may also be referred to as the radiation opening. For example, this opening may be surrounded by an edge of the housing. The opening may have a round cross section, for example a circular cross section, other cross section geometries also being conceivable, however, for example polygonal cross sections or other, non-round cross sections. The transducer core may have, for example, a radiation surface via which ultrasonic signals may be transmitted from the transducer core to the fluid medium or via which ultrasonic signals may be absorbed from the fluid medium by the transducer core. This radiation surface may be situated, for example, on the same plane as the edge of the housing.

Alternatively, however, the transducer core may also, in principle, project slightly over the plane of the housing edge into the fluid medium, or it may be set back into the housing interior in relation to the housing edge in such a way that the radiation surface and the edge of the housing are not necessarily, yet which may be, situated on the same plane.

In the method, the opening is at least partially sealed by a sealing film. It is proposed to carry out the method in such a way that the at least one sealing film is stretched and is connected to the housing in the stretched state in such a way that the sealing film at least partially seals the opening. The stretching of the sealing film may take place, in principle, before or during the sealing of the opening. The stretched state of the sealing film may be maintained even after connection to the housing, it also being possible, however, to release the film during or after connection.

A sealing film is generally understood to be a film-like element, i.e., an element whose thickness is designed to be substantially less than its lateral dimensions, for example by a factor of at least 10, which may be by a factor of at least 100, in particular by a factor of at least 1,000 or even 10,000. The sealing film may have sealing properties and ensures an at least partial seal of an inner space of the housing in which the transducer core is at least partially accommodated against the fluid medium, for example in combination with other components of an optional sealing element. For example, the sealing film may have a thickness of less than 200 µm. Sealing film thicknesses of less than 100 µm may particularly be used, in particular thicknesses of less than 50 µm may be used and, in an especially particular manner, advantageously may be less than 25 µm, to ensure a good coupling between the transducer core and the fluid medium on the one hand, and to achieve the least possible transmission of structure-borne noise between the transducer element and the housing, on the other hand.

Stretching the sealing film is understood to be a mechanical effect on the sealing film in which a force, which may be a tensile force, is applied to the sealing film at least in a direction parallel to the lateral extension of the sealing film. In particular, an expansion of the sealing film in at least one direction parallel to the lateral extension of the sealing film may be achieved, for example an elastic and/or a plastic stretching. The sealing film may be stretched in at least two directions parallel to the lateral extension of the sealing film, which may be in two directions oriented perpendicularly to each other.

The sealing film may be connected to the housing, in particular, on a housing edge. For example, this edge may be a circumferential housing edge to which the sealing film is at least partially attached, so that the sealing film at least partially, which may be completely, seals the opening. For example, this edge may be a flat edge. The connection between the housing and the sealing film may be established, in principle, in a force-fit manner and/or a form-locked manner and/or by an integral joint. The sealing film may be furthermore also connected to a radiation surface of the transducer core.

In principle, the sealing film may be made of at least one film material of any type, for example a metallic material, a plastic material or even a multi-layer material or combinations of the aforementioned materials and/or other materials. The sealing film may include at least one thermoplastic plastic material or is made entirely of a thermoplastic plastic material of this type. The housing and the sealing film may generally have at least one identical material or be at least partially made of at least one identical material. Both the sealing film and the housing may be made of the same material at least in the area of the housing edge. In particular, the material may be a thermoplastic plastic material.

In particular, one or more of the following thermoplastic plastic materials may be used as thermoplastic plastic materials for the sealing film and may also be for the housing, at least in the area of the housing edge and/or the opening: polymethyl methacrylate (PMMA); polyvinyl fluoride (PVF, for example "Tedlar® ES"); polyether ketone, in particular polyether ether ketone (PEEK); polyamide imide (PAI); liquid crystal polymer (LCP, for example "Vectra® LCP" from Ticona); polyether sulfone (PES); polysulfone (PSU); polyphenylene sulfide (PPS). A combination of the aforementioned materials and/or other materials is also conceivable. The sealing film may furthermore contain other materials, for example as a coating and/or as part of a laminate structure. Other materials may also be used, in principle.

The sealing film may be connected to the housing and may also be connected to the transducer core, in particular, using a thermal connecting method, which may be under the impact of heat and pressure. The connection to the housing and optionally to the transducer core may be carried out simultaneously, for example in a single operation and/or with the aid of a tool. For example, heat may be applied during the thermal connecting process by heating via a tool and/or by ultrasonic irradiation and/or by laser irradiation and/or by infrared irradiation. In general, when establishing the connection between the sealing film and the housing and/or transducer core, in particular, a connecting method may be used which is selected from: a hot pressing method; a hot stamping method; an ultrasonic welding method; a laser welding method. However, a combination of the aforementioned methods and/or other methods may also be used, in principle. The connection between the sealing film and the housing and which may also be to the transducer core may be carried out, in particular, without adhesive. Although an edge and/or a gap on the edge of the sealing film between the housing and the sealing film may be sealed in principle, it may be, however, omitted.

The sealing film may be stretched, in particular, with the aid of at least one stretching frame, i.e., using a stretching frame and optionally one or more additional elements. A stretching frame is understood to be a stretching tool of an at least partially frame-like design, which may have a circumferential design but which may also be designed as an interrupted frame. For example, the stretching frame may have at least one frame component and at least one second frame component, the sealing film or a sealing film sheet being introduced into the opened stretching frame parts. In principle, the film may be introduced into and stretched in the stretching frame while the sealing film sheet is in the unstretched state or in a state in which it is already pre-stretched in at least one dimension. The stretching frame parts may then be pressed together to stretch the sealing film sheet or fix it in place. The stretched state may then be produced or intensified within the stretching frame by applying additional forces to the sealing film sheet, for example by applying force perpendicularly to the lateral extension of the sealing film sheet in the stretching frame. This may be carried out, in particular, by pressing the housing or the housing edge and/or the transducer core onto the sealing film sheet and/or pressing it/them into the sealing film sheet or vice versa. Since the sealing film sheet is attached to the stretching frame, this pressing action produces a stretched state or, if a pretension already exists, an intensification of the stretched state of the sealing film sheet.

A sealing film sheet is understood to be a film sheet of the sealing film material which has a greater dimension in the lateral direction than the actual sealing film which seals the opening in the finished state of the ultrasonic transducer. However, no further distinction is made below between the terms sealing film sheet and sealing film. For example, the sealing film sheet may have larger dimensions in at least one lateral dimension than the later sealing film. The sealing film may have, for example, a round and/or polygonal cross section, depending on the cross section of the housing opening. The sealing film may be separated from a sealing film sheet remaining in the stretching frame during and/or after connection to the housing and which may be also during and/or after connection to the transducer core. The remaining sealing film sheet thus represents the cut section from which the actual sealing film may be separated, which may take place during and/or after connection to the housing and which may be also to the transducer core. The sealing film may be connected to multiple housings at the same time, multiple sealing films for multiple ultrasonic transducers being simultaneously produced from the sealing film sheet clamped in the stretching frame. The sealing film may be separated from the sealing film sheet, in particular, with the aid of a separating method which may be selected from: a punching method; a stamping method; a cutting method, in particular a laser cutting method. However, other separating methods and/or combinations of the aforementioned and/or other separating methods may be used, in principle.

The sealing film may be pressed against the housing and which may be also against the transducer core, in particular, with the aid of at least one tool. This means that either a force is applied to the film in the direction of the housing and/or a force is applied to the housing in the direction of the sealing film in such a way that a close physical contact is established between these elements. As described above, this application of force may also be used to establish and/or intensify the stretched state. The tool may be simultaneously configured to separate the sealing film from the sealing film sheet remaining in the stretching frame during and/or after connection to the housing. For this purpose, the tool may have, for example, a corresponding contour and/or a corresponding cutting edge. For example, the tool may include one or more projections with the aid of which a separation may be effected. At the same time, the tool may also be configured to transfer heat to the sealing film and/or the housing. For example, the tool may be designed as a hot stamping tool. The tool may be designed, in particular, in at least two parts and include at least one first tool part and at least one second tool part. The at least one tool part may be configured to fix the housing and/or the transducer core in place, and the at least one second tool part may be configured to press the sealing film against the housing and which may be against the transducer core. As described above, the pressing action may take place from the direction of the housing and/or from the direction of the sealing film.

In addition to the method described above in one or more of the method variants described above, an ultrasonic transducer for use in a fluid medium is furthermore proposed which may be manufactured according to a method according to one or more of the embodiments described above. The ultrasonic transducer is designed in such a way that the sealing film is stretched. As illustrated above, however, the method itself may be carried out, in principle, in such a way that the sealing film is released during and/or after connection to the housing.

Using the proposed method in one or more of the variants described above, a cost-effective and reliable connection of the sealing film to the ultrasonic transducer housing is guaranteed. In particular, ultrasonic transducers used for measuring ultrasonic air masses in internal combustion engines may be implemented in this manner. However, other applications for ultrasonic transducers may be provided with reliable ultrasonic transducers in this manner, for example distance sensors, fill level sensors or other applications within or outside automotive engineering. In principle, known ultrasonic transducers may be easily manufactured or modified. For example, the ultrasonic transducer may include a piezoceramic and an impedance matching body and a sealing film. In particular, the housing may be implemented as a plastic carrier part, for example as a frame, as a ring or as a cup. The housing may be designed, in principle, as a single piece but may also be designed as multiple parts. For example, the housing may include other elements above the actual housing part which is connected to the sealing film, for example elements which completely or partially seal the back of the housing, i.e., on the side facing away from the fluid medium.

In a particular manner, the housing and the sealing film are at least partially made of thermoplastic plastics, which are easy to process. The sealing film may be attached to the housing and/or to a plastic carrier part of the housing by pressing the sealing film onto the housing, which may be without additional adhesive, under the effect of heat, for example in the form of ultrasonic welding, hot pressing or laser welding. Connecting techniques of this type are known, in principle. If necessary, the sealing film may also be optionally attached to the transducer core in the same manner, in particular to an impedance matching body of the transducer core.

The proposed connecting methods make it possible to omit adhesive lamination of the sealing film. Due to the local heat effect, the sealing film, in particular, may expand, while the housing, in particular the plastic carrier part of the housing, expands to a lesser degree. This enables the sealing film to be applied in a stretched manner without wrinkling, which is extremely advantageous for a radiation characteristic of the ultrasonic transducer. If necessary, it may also be possible to omit additional sealing of the edges of the sealing film using adhesive, since the connection, for example a welded connection, between the sealing film and the housing may be designed to be intrinsically media-tight, in particular if the same materials are used in the area of the connection.

Examples of ultrasonic transducers that may be modified according to the present invention (within the scope of the present invention) are discussed in DE 203 02 582 U1, EP 0 766 071 A1 or in DE 10 2007 010 500 A1.

Exemplary embodiments of the present invention are illustrated in the figures and explained in greater detail in the following description.

BRIEF DESCRIPTION OF THE DRAWINGS

FIGS. 5A, 5B, 5C, 5D, and 5E show subsequent processing of an intermediate product of an ultrasonic transducer manufactured according to FIG. 4.

FIGS. 6A, 6B, 6C, and 6D show method steps for separating the sealing film from a sealing film sheet.

FIGS. 7A, 7B, and 7C show exemplary embodiments of contours of a housing edge and a second tool part as alternatives to FIGS. 6A, 6B, 6C, and 6D.

DETAILED DESCRIPTION

Figure 1:
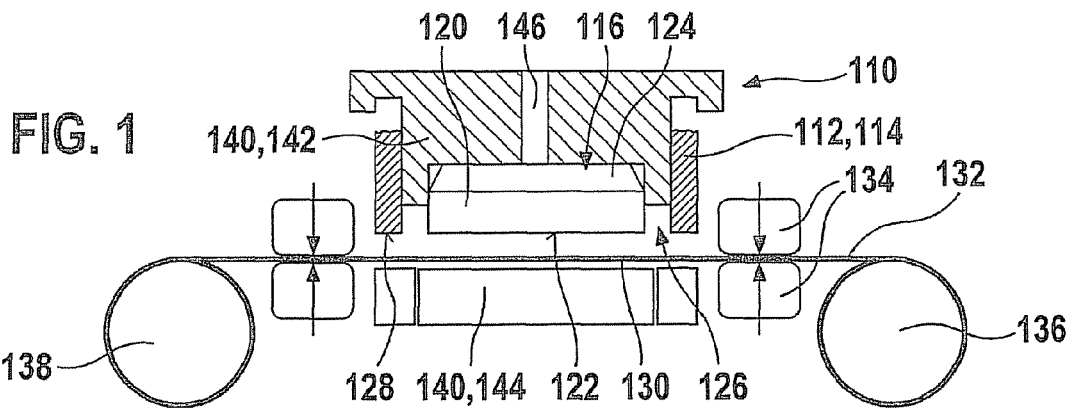
FIGS. 1, 2, 3, and 4 show a schematic sequence of a method according to the present invention for manufacturing an ultrasonic transducer.

FIGS. 1 through 4 show method steps of a manufacturing process for manufacturing an ultrasonic transducer or an intermediate product of an ultrasonic transducer in a schematic sectional representation. The method may include additional method steps, so that no further distinction is made between the intermediate product and the actual ultrasonic transducer, so that reference numeral 110 is used in the figures to identify both the ultrasonic transducer itself and its intermediate products.

Ultrasonic transducer 110 generally has a housing 112. This housing 112 may include, for example, a housing support part 114, and it may be designed as a single piece or as multiple pieces. At least one transducer core 116 is introduced into housing 112 at one or more points in time during the method, not necessarily at the point in time in the illustrated exemplary embodiments. In the exemplary embodiment illustrated in FIGS. 1 through 5E, this transducer core 116 is initially incomplete, and it is completed by an electric-acoustic transducer element, for example a piezoelectric element, only in method step 5C. Other embodiments are also possible, for example in that transducer core 116 is fully accommodated in housing 112 from the very beginning, or in that the transducer core is introduced into housing 112 in a different way and/or at different points in time and/or in a different combination. With regard to transducer core 116, no distinction in terminology is thus made between actual transducer core 116 and its intermediate products. For example, transducer core 116 includes not only aforementioned electric-acoustic transducer element 118 in the finished state of ultrasonic transducer 110, but also an impedance matching body 120 for matching the impedance, which has a radiation surface 122 facing the fluid medium, for example a λ/4 layer, as well as at least one optional thermal compensating element 124 for compensating thermal stresses between impedance matching body 120 and electric-acoustic transducer element 118.

In its finished state, housing 112 has an opening 126 on its side facing the fluid medium, it being possible for this opening to be surrounded by a housing edge 128 in the illustrated exemplary embodiment (see FIG. 1). In the method described in FIGS. 1 through 4, this opening 126 is sealed by a sealing film 130, sealing film 130 being connected to housing edge 128 and optionally also to radiation surface 122 of transducer core 116 using a connecting method. Sealing film 130 is initially part of a sealing film sheet 132 and is separated from this sealing film sheet 132 during and/or after sealing film 130 is connected to housing 112 (see FIG. 4).

FIG. 1 shows that sealing film 130 may be initially drawn through a stretching frame 134, for example with the aid of two rollers 136, 138. For example, roller 138 may be designed as a winding-off roller and roller 136 as a winding-up roller, in particular in the direction of rotation of rollers 136, 138 shown in FIG. 4. After sealing film sheet 132 is introduced into stretching frame 134, stretching frame 134 is closed as shown in FIG. 1. A tool 140 is furthermore used which includes a first tool part 142 and a second tool part 144. In the illustrated exemplary embodiment, first tool part 142 is used to fix housing 112, and may also be used to fix transducer core 116, in place. Housing 112, or housing support part 114 and transducer core 116 or impedance matching body 120 and optionally thermal compensating element 124, may form a coupling module. First tool part 142 may be adapted, for example, to the geometry of this coupling module, and it may be designed, for example, entirely or partially as a gripper and/or in a different manner to grip the coupling module and/or parts thereof and/or fix it/them in place. For example, a vacuum holder may also be provided, as indicated by an optional vacuum channel 146 in FIGS. 1 through 4. With the aid of first tool part 142, the coupling module is placed on sealing film sheet 132 within stretching frame 134. Housing 112 (at least in the area of housing support part 114) and sealing film sheet 132 may be made of a thermoplastic plastic material, for example PMMA, PVF, PEEK, PAI, LCP, PES, PSU or PPS. Sealing film sheet 132 may optionally include additional materials, for example as a coating, and it should be thinner than approximately 200 μm, which may be thinner than 50 μm and, in particular, which may be thinner than 25 μm, depending on the material used.

Figure 2:
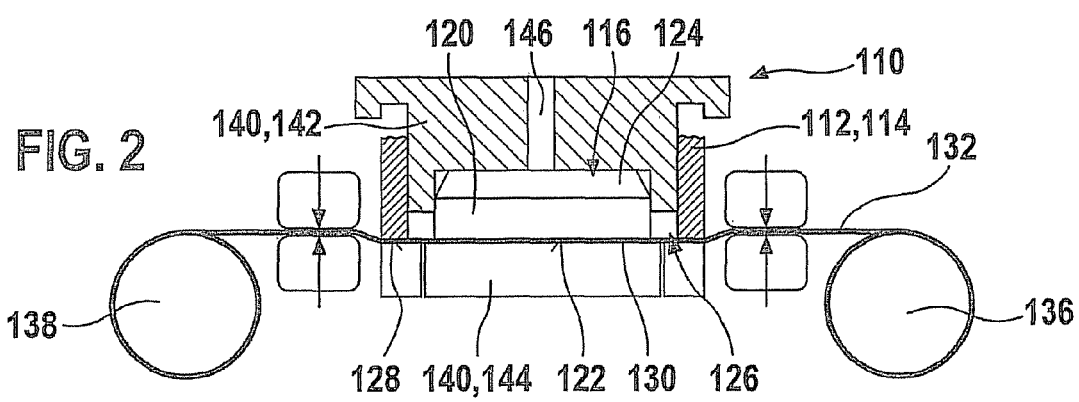

As shown in FIGS. 1 through 4, second tool part 144 is situated within stretching frame 134 below sealing film sheet 132, i.e., on the side of sealing film sheet 132 diametrically opposed to first tool part 132. FIG. 2 shows a method step in which housing 112 or the coupling module is pressed downward with the aid of first tool part 142, for example with the aid of the gripper and/or a first tool half, i.e., in the direction of second tool part 144. This stretches the film and presses it onto second tool part 144. This exemplary embodiment shows that, in the present example of the method as well as in other exemplary embodiments of the proposed method, sealing film 130 may be stretched before, during or after sealing film sheet 132 has been introduced into stretching frame 134. The stretching action may take place independently of the pressing of housing 112 onto sealing film sheet 132 or, as an alternative or in addition, the stretching action may take place by pressing housing 112 or housing edge 128 onto sealing film sheet 132, for example within stretching frame 134, which is able to fix sealing film sheet 132 in place. Second tool part 144 may be designed, in particular, to be heated, and it may act as a base in order to build up a counter-pressure. By pressing sealing film 130 and housing edge 128 onto each other in this manner, sealing film 130 and housing 112 may be integrally joined to each other in the area of housing edge 128, thereby producing the effect of a welding process and/or a hot stamping process.

Figure 3:
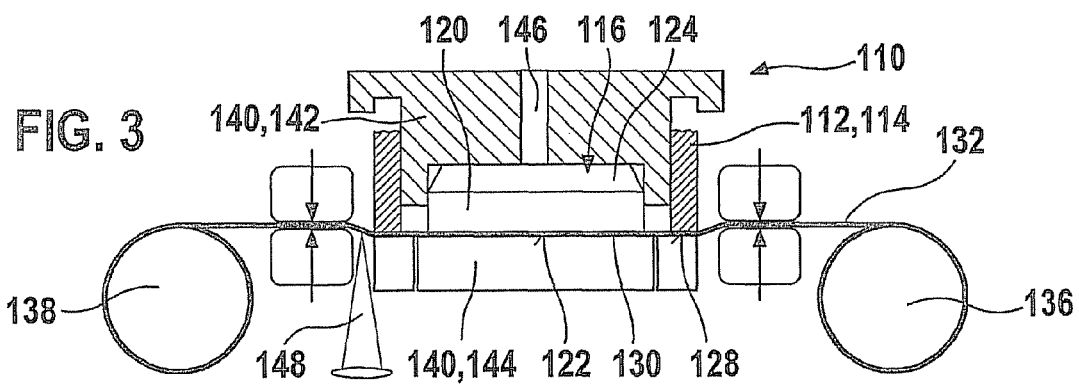

In a method step illustrated in FIG. 3, sealing film 130 is separated from remaining sealing film sheet 132. FIG. 3 shows an exemplary embodiment in which sealing film 130 is separated from the rest of sealing film sheet 132 by a laser 148. However, other separation methods may also be used as an alternative or in addition. The separation may take place, for example, on housing edge 128 or, as shown in FIG. 3, outside housing edge 128, for example directly on an outer rim of housing edge 128.

Figure 4:
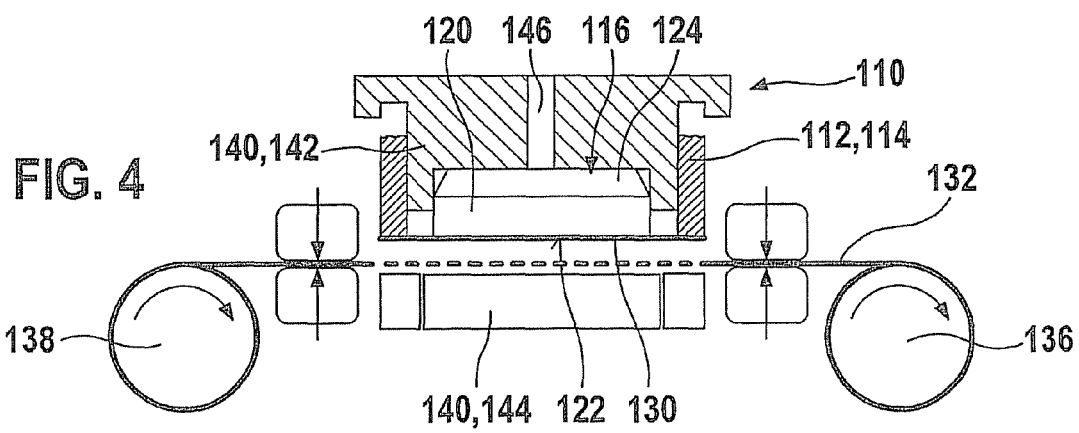

Finally, FIG. 4 shows how the intermediate product of ultrasonic transducer 110 manufactured in this manner, i.e., the module manufactured in this manner, including housing 112 and housing carrier part 114, the coupling module and sealing film 130, is removed from stretching frame 134, so that sealing film sheet 132 may be uncoiled for manufacturing the next ultrasonic transducer 110.

However, multiple ultrasonic transducers 110 may also be optionally manufactured at the same time within a stretching frame 134, or openings 126 in this ultrasonic transducer 110 may be sealed at the same time.

FIGS. 5A through 5E show subsequent processing of the intermediate product of ultrasonic transducer 110 obtained according to FIG. 4. FIG. 5A initially shows the module of ultrasonic transducer 110 obtained after the method step according to FIG. 4. A gap 150 may be located between transducer core 116 or the coupling module and housing 112. This gap 150 may be optionally filled with a separate material, as shown in FIG. 5B, which is also referred to as decoupling material 152. It is also possible to partially fill gap 150 with decoupling material 152. Decoupling material 152 may be configured, for example, to stabilize transducer core 116 and/or the coupling module for further handling and/or to provide a decoupling or compensating element in the later ultrasonic transducer 110. Decoupling material 152 may include, for example, a foam material and/or a silicone, and it may be filled by an LSR injection process (LSR: liquid silicone rubber) in a suitable tool. The separation of sealing film 130 from sealing film sheet 132, for example with the aid of laser 148 and/or another separating tool, may take place, if necessary, only after this filling process, in which decoupling material 152 is introduced into gap 150, for example after the LSR process or even after other construction steps. In this case, the partial construction stages of the transducer, for example after the method step according to FIG. 2, may initially remain in use on sealing film sheet 132. Various other embodiments are possible.

FIG. 5C shows a method step in which electric-acoustic transducer element 118, for example a piezoelectric element, is introduced into transducer core 116, for example by gluing this electric-acoustic transducer element 118 onto thermal compensating element 124. FIG. 5D shows a method step in which electric-acoustic transducer element 118 is electrically contacted using a contacting arrangement 154, for example with the aid of appropriate contact wires. FIG. 5E shows a method step in which the remaining inner space of housing 112 is completely or partially filled with a damping and/or decoupling casting compound 156.

As described above, transducer core 116 may include impedance matching body 120, i.e., at least one material which promotes acoustic coupling between electric-acoustic transducer element 118, for example the piezoelectric element, and the fluid medium or measuring medium. In the case of gaseous media, a low-density material is advantageous, for example a foamed and/or syntactic plastic, for example an epoxy resin and hollow glass spheres, porous polyamide or PEEK. The coupling module may also include a further area in the form of thermal compensating element 124, which has a different density. This further area may be used, for example, to further improve the acoustic matching and/or to protect the piezoelectric element or electric-acoustic transducer element 118 from thermally induced twisting. Furthermore, transducer core 116 may include other elements. Decoupling material 152, or in general a material within gap 150 and surrounding coupling module or transducer core 116, may also be omitted or, for example, it may be designed to be entirely or partially identical to casting compound 156.

The connection between sealing film 130 and housing 112 and optionally also transducer core 116 or radiation surface 122 may be established in different ways, for example using a thermal connection. The heat needed for the connection may be generated, for example, by infrared and/or laser radiation and/or by friction and/or vibrations as an alternative or in addition to using a heated second tool part 144 or a heated base and/or a stamp.

FIGS. 6A through 6D show method steps which may completely or partially replace the method steps according to FIGS. 2 and 3. Thus, these figures show a method variant in which the used second tool part 144, for example the used pressing stamp, has one or more additional contours 158 in addition to a connection of sealing film 130 to housing 112 or a housing sleeve, for example by welding. For example, these contours 158 may include one or more projections and/or one or more indentations, for example in an otherwise flat surface of second tool part 144. One or more indentations and/or projections may also be optionally provided in housing edge 128, or counter-contours of this type having one or more projections and/or one or more indentations may be produced only upon pressing second tool part 144 onto housing edge 128. In this manner, second tool part 144 may be designed, for example, to at least partially press sealing film 130 into housing 112, into housing edge 128 and/or into counter-contours, for example into one or more indentations in housing 112. This is illustrated in FIG. 6A. In addition to the force-fit or integral joint, this may result in a form-lock which may further stabilize the connection between sealing film 130 and housing 112. At the same time, sealing film 130, which is still part of sealing film sheet 132 in FIG. 6A, is selectively pre-damaged, for example at the lowest point and/or at other points in the area in which it is pressed into housing 112, so that sealing film 130, for example in this area, may be easily undone by laser radiation 148 (see FIG. 6B) and/or by another separating method, to separate sealing film 130 from sealing film sheet 132 and to separate ultrasonic transducer 110.

Residual film 160, which faces outward, i.e., the remaining portion of sealing film sheet 132, adheres to housing edge 128 only over a very small surface area and may be easily torn off, so that no film remnants of sealing film 130 or of sealing film sheet 132 project over housing 112 or housing edge 128. This is shown in FIG. 6C, which illustrates ultrasonic transducer 110 after it has been separated.

If necessary, an indentation 162 in housing edge 128 and/or another type of counter-contour to contour 158 in housing edge 128 may also be completely or partially covered and/or filled by an adhesive bead and/or another filling material. For example, an edge of sealing film 130 may be sealed in this manner. As an alternative or in addition, for example, the laser cutting may be replaced by a punching operation and/or by another separating operation. This may be done, for example, either after hot pressing or concurrently with hot pressing according to FIG. 6A, for example, by forming contour 158 indicated in FIG. 6A to have sufficiently small radii and/or sharp edges in the heated base or in second tool part 144, for example, by providing contour 158 to have a corresponding design, for example with the aid of one or more sharp edges. For example, sealing film 130 may also be preheated in this or another process prior to the connecting process, for example using a hot air blower and/or using an infrared heater. The same applies optionally to the other parts to be joined, i.e., housing 112 or housing edge 128 and/or transducer core 116, which may also be preheated as an alternative or in addition.

As an alternative or in addition to using a stretching frame 134, the contouring of housing edge 128 and/or second tool part 144 may be used to stretch sealing film 130 in that pressing the film into and/or pulling it around the contours of housing edge 128 and/or second tool part 144 increases this tension or, produces it in the first place.

Further examples of such contour formation of a contour 158 in second tool part 144 and/or of a counter-contour 164 of the housing edge are illustrated in FIGS. 7A through 7C. FIG. 7A shows an exemplary embodiment in which an indentation 162 is provided in housing edge 128 as a counter-contour 164 and, as an alternative or in addition, an elevation 166 is provided in second tool part 144 as contour 158. This exemplary embodiment may thus, in principle, correspond to the example in FIG. 6A. Indentation 162 and/or elevation 166 may be provided, in principle, with a rounded design, as shown, for example, in FIG. 6A, and/or they may be provided with a polygonal design, for example having a rectangular cross section. Mixed forms are also possible. In the example illustrated in FIG. 7A, for example, indentation 162 has a rectangular design, and elevation 166 is rounded. However, other embodiments are also possible. Corresponding elevations and indentations may also be distributed to housing edge 128 and second tool part 144 in a manner other than shown in FIG. 7A. For example, FIG. 7B shows an example in which an elevation 166 is provided in housing edge 128, and a corresponding indentation 162 is provided in second tool part 144. The above discussion with regard to FIG. 7A applies similarly to the shapes of indentation 162 and elevation 166. The contours of second tool part 144 and/or housing edge 128 may also be provided with a more complex design. Thus, second tool part 144 and/or housing edge 128 may each have, for example, combinations of one or more elevations 166 and/or indentations 162 and/or one or more stepped contours. Such an example is illustrated in FIG. 7C. In this case, second tool part 144 includes an indentation 162. Housing edge 128 includes a stepped contour which includes, by way of example, an elevation 166 corresponding to indentation 162 in second tool part 144 and optionally an indentation 162. Various other embodiments are also possible.

What is claimed is:

1. A method for manufacturing an ultrasonic transducer for use in a fluid medium, the method comprising:
   stretching at least one sealing film connected to at least one housing of the ultrasonic transducer, so that in a stretched state, the at least one sealing film at least partially seals an opening;
   wherein the ultrasonic transducer includes at least one transducer core which has at least one acoustic-electric transducer element, the ultrasonic transducer also including the at least one housing which at least partially surrounds the transducer core and which has at least one opening facing the fluid medium.

2. The method of claim 1, wherein the sealing film is also connected to a radiation surface of the transducer core.

3. The method of claim 1, wherein the sealing film includes a thermoplastic plastic material.

4. The method of claim 1, wherein the housing and the sealing film have at least one identical material, which includes a thermoplastic plastic material.

5. The method of claim 1, wherein the sealing film is connected to the housing and also to the transducer core using a thermal connecting process.

6. The method of claim 5, wherein the thermal connecting process includes one of a hot pressing process, a hot stamping process, an ultrasonic welding process, and a laser welding process.

7. The method of claim 1, wherein the connection between the sealing film and the housing and also to the transducer core may be provided without an adhesive.

8. The method of claim 1, wherein the sealing film is stretched with a stretching frame.

9. The method of claim 8, wherein the sealing film is separated from a sealing film sheet remaining in the stretching frame at least one of during and after connection to the housing and also at least one of during and after connection to the transducer core.

10. The method of claim 9, wherein separation is carried out with a separating process, which includes one of a punching process, a stamping process, a cutting process, and a laser cutting process.

11. The method of claim 1, wherein the sealing film is pressed against the housing and also against the transducer core with a tool.

12. The method of claim 11, wherein the tool is configured to separate the sealing film from the sealing film sheet remaining in the stretching frame at least one of during and after connection to the housing.

13. The method of claim 11, wherein the tool has at least a two-part configuration, in which at least one first tool part is configured to fix at least one of the housing and the transducer core in place, and in which at least one second tool part is configured to press the sealing film against the housing and against the transducer core.

14. An ultrasonic transducer for use in a fluid medium, comprising:
   at least one transducer core which has at least one acoustic-electric transducer element;
   at least one housing which at least partially surrounds the transducer core and which has at least one opening facing the fluid medium; and
   at least one sealing film connected to the at least one housing of the ultrasonic transducer, so that in a stretched state, the at least one sealing film at least partially seals an opening.

* * * * *